US009235869B2

(12) United States Patent
Greenman et al.

(10) Patent No.: US 9,235,869 B2
(45) Date of Patent: Jan. 12, 2016

(54) METHOD AND SYSTEM FOR TRACKING GOODS

(71) Applicants: Eric Greenman, Scottsdale, AZ (US); Bo E. H. Saxberg, Oro Valley, AZ (US)

(72) Inventors: Eric Greenman, Scottsdale, AZ (US); Bo E. H. Saxberg, Oro Valley, AZ (US)

(*) Notice: Subject to any disclaimer, the term of this patent is extended or adjusted under 35 U.S.C. 154(b) by 224 days.

(21) Appl. No.: 13/710,167

(22) Filed: Dec. 10, 2012

(65) Prior Publication Data

US 2014/0095187 A1  Apr. 3, 2014

Related U.S. Application Data

(63) Continuation-in-part of application No. 13/278,746, filed on Oct. 21, 2011, now Pat. No. 8,332,237, which is a continuation of application No. 11/908,397, filed as application No. PCT/US2006/009058 on Mar. 13, 2006, now Pat. No. 8,078,479.

(60) Provisional application No. 60/660,780, filed on Mar. 11, 2005.

(51) Int. Cl.
*G06Q 10/08* (2012.01)
*G06Q 50/22* (2012.01)
*G06F 19/00* (2011.01)

(52) U.S. Cl.
CPC ............ *G06Q 50/22* (2013.01); *G06F 19/3456* (2013.01); *G06Q 10/08* (2013.01)

(58) Field of Classification Search
CPC .......................................... G06Q 50/22–50/24
See application file for complete search history.

(56) References Cited

U.S. PATENT DOCUMENTS 5,628,530 A * 5/1997 Thornton ............... B42D 12/00 283/67
5,797,515 A * 8/1998 Liff ..................... G06F 19/3462 221/129
5,832,449 A * 11/1998 Cunningham ......... G06K 17/00 705/2
5,845,255 A * 12/1998 Mayaud .............. G06F 19/3456 705/3
5,845,264 A * 12/1998 Nellhaus ............. G06F 19/3462 235/375
6,021,392 A * 2/2000 Lester ................... G06F 19/326 705/2
6,055,507 A * 4/2000 Cunningham ......... G06K 17/00 705/2
6,067,524 A * 5/2000 Byerly ................... G06Q 30/02 705/14.1
6,098,892 A * 8/2000 Peoples, Jr. ......... G06F 19/3462 235/462.01
6,152,364 A * 11/2000 Schoonen ............. G06F 19/323 221/7
6,155,485 A * 12/2000 Coughlin .............. G06F 19/322 235/383

(Continued)

OTHER PUBLICATIONS

Business/Health & Science Editors. "IMS Health Strategic Technologies Launches SampleTrak". Business Wire. New York: Apr. 19, 2000. p. 1.*

(Continued)

*Primary Examiner* — Robert Sorey
(74) *Attorney, Agent, or Firm* — Schmeiser, Olsen & Watts LLP

(57) ABSTRACT

A method and system for tracking goods is provided wherein the system is a transnomic code system. The transnomic code system includes a prescriber interface, a pharmaceutical interface, a pharmacy interface and a management server that communicate via communication mediums, such as an electronic prescribing switch and the Internet. The transnomic code is a dynamic code that includes a tracking code and one or more information sets, wherein each information set includes a read header and extensible content. The transnomic code is assigned to a product, such as a pharmaceutical product. The system allows for adding information sets to the transnomic code at any point during the life-cycle of a product.

11 Claims, 6 Drawing Sheets

(56) References Cited

U.S. PATENT DOCUMENTS

| | | | | |
|---|---|---|---|---|
| 6,170,746 B1* | 1/2001 | Brook | G06F 19/3462 | 235/385 |
| 6,202,923 B1* | 3/2001 | Boyer | G06F 19/3462 | 235/375 |
| 6,260,761 B1* | 7/2001 | Peoples, Jr. | G06K 7/14 | 235/375 |
| 6,561,977 B2* | 5/2003 | Williams | G06F 19/322 | 128/920 |
| 6,654,724 B1* | 11/2003 | Rubin | G06F 19/322 | 705/2 |
| 6,687,676 B1* | 2/2004 | Denny | G06F 19/3456 | 705/2 |
| 6,755,784 B2* | 6/2004 | Williams | G06F 19/322 | 128/920 |
| 6,859,780 B1* | 2/2005 | Cunningham | G06K 17/00 | 235/375 |
| 6,877,658 B2* | 4/2005 | Raistrick | G06K 7/0008 | 235/385 |
| 6,892,941 B2* | 5/2005 | Rosenblum | G06Q 10/10 | 235/375 |
| 7,058,584 B2* | 6/2006 | Kosinski | G06F 19/3418 | 379/106.02 |
| 8,332,237 B2* | 12/2012 | Greenman | G06F 19/3456 | 705/2 |
| 2002/0013787 A1* | 1/2002 | Pollard | G06Q 10/10 | 715/223 |
| 2002/0032582 A1* | 3/2002 | Feeney, Jr. | G06F 19/3462 | 705/2 |
| 2002/0161607 A1* | 10/2002 | Subich | G06F 19/322 | 705/3 |
| 2003/0212577 A1* | 11/2003 | Nichtberger | G06Q 50/22 | 705/2 |
| 2003/0216831 A1* | 11/2003 | Hart | G06F 19/322 | 700/235 |
| 2003/0216974 A1* | 11/2003 | Browne | G06F 19/327 | 705/28 |
| 2004/0148195 A1* | 7/2004 | Kalies | G06F 19/322 | 705/2 |
| 2004/0205343 A1* | 10/2004 | Forth et al. | | 713/168 |
| 2004/0236607 A1* | 11/2004 | Kost | G06Q 10/10 | 705/2 |
| 2004/0236630 A1* | 11/2004 | Kost | G06Q 30/02 | 705/14.13 |
| 2005/0010448 A1* | 1/2005 | Mattera | G06Q 10/10 | 705/3 |
| 2005/0033610 A1* | 2/2005 | Cunningham | G06K 17/00 | 705/2 |
| 2005/0038673 A1* | 2/2005 | Stookey | G06Q 50/22 | 705/2 |
| 2005/0060199 A1* | 3/2005 | Siegel | G06F 19/322 | 705/2 |
| 2006/0224417 A1* | 10/2006 | Werner | G06F 19/366 | 705/2 |
| 2008/0022005 A1 | 1/2008 | Wu et al. | | |
| 2008/0208626 A1 | 8/2008 | Greenman | | |
| 2010/0268550 A1* | 10/2010 | Abuzeni et al. | | 705/3 |
| 2012/0041787 A1* | 2/2012 | Greenman | G06F 19/3456 | 705/2 |
| 2012/0166215 A1* | 6/2012 | Choi et al. | | 705/2 |
| 2012/0290314 A1* | 11/2012 | Putnam et al. | | 705/2 |

OTHER PUBLICATIONS

Business Editors/High-Tech Writers. "Synergistix Introduces C.A.T.S. Tablet PC Edition", Business Wire. New York: Mar. 7, 2003. p. 1.*

* cited by examiner

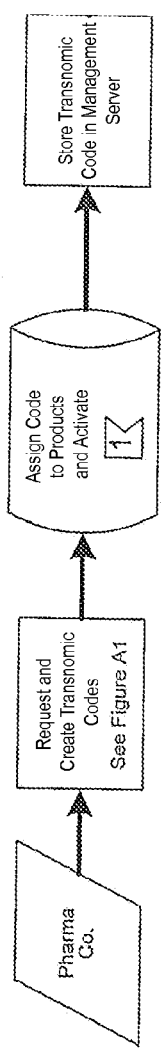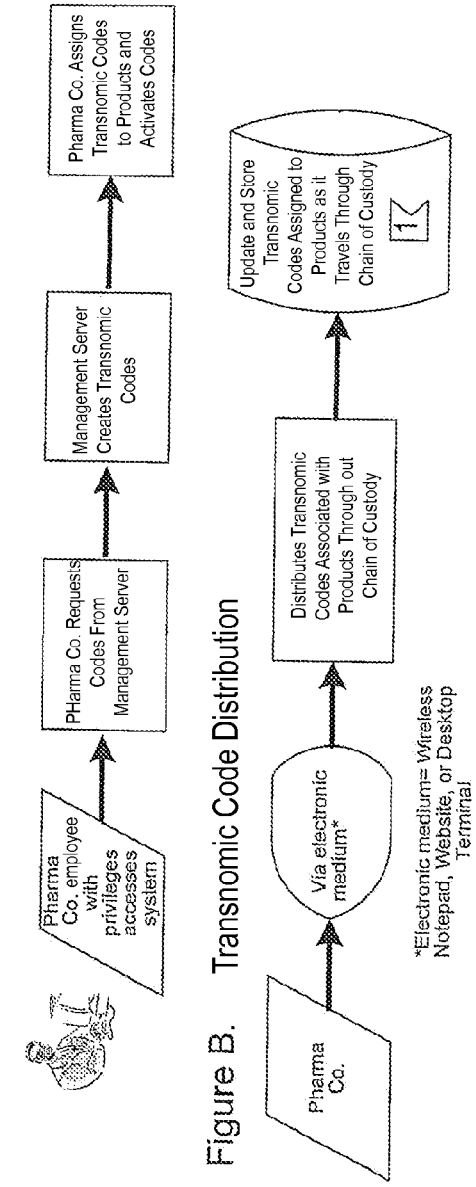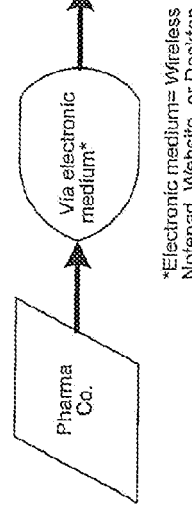

TRANSNOMIC CODES
Figure C. Transnomic Codes Used By a Physician/Prescriber (Via Electronic Medium)
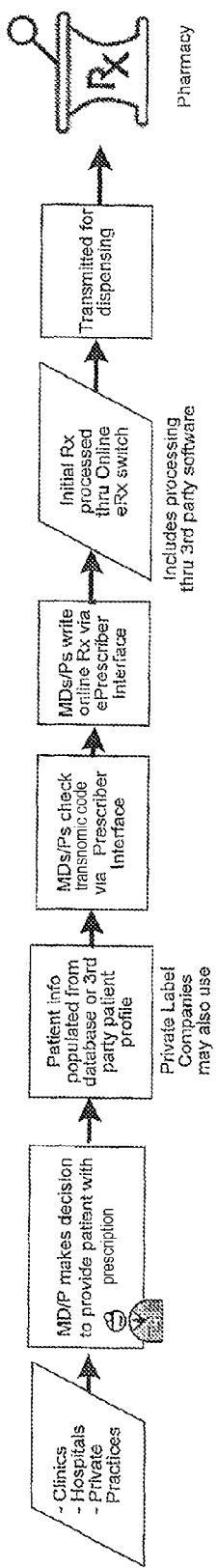
Figure D. Transnomic Codes Used By a Physician/Prescriber (Manual Process)
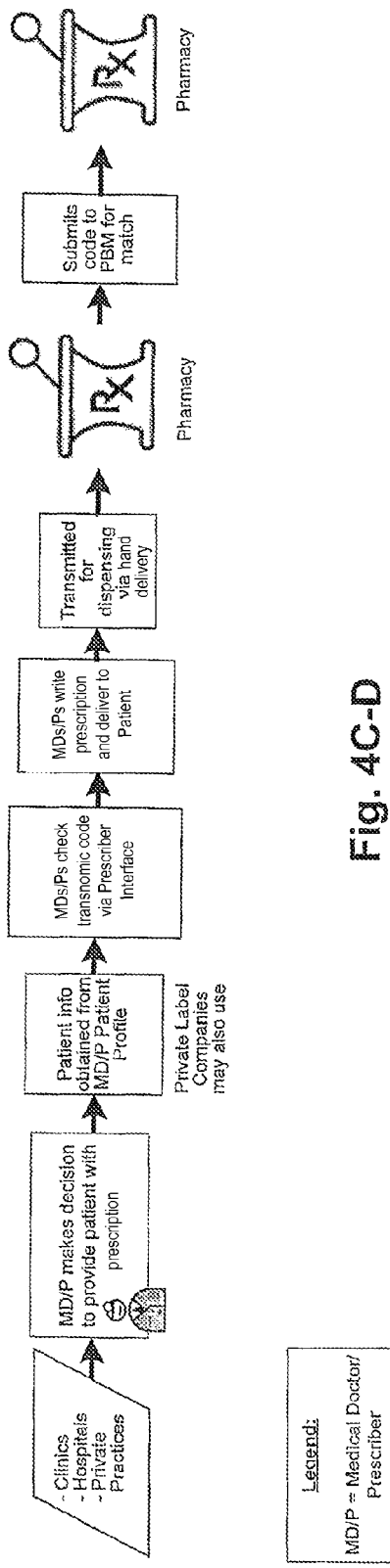
Fig. 4C-D
Legend:
MD/P = Medical Doctor/Prescriber

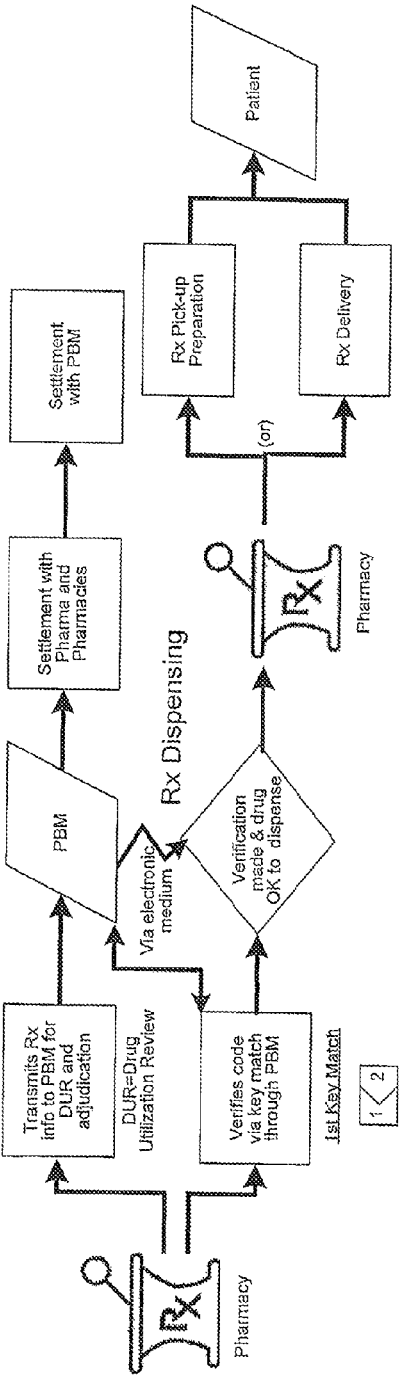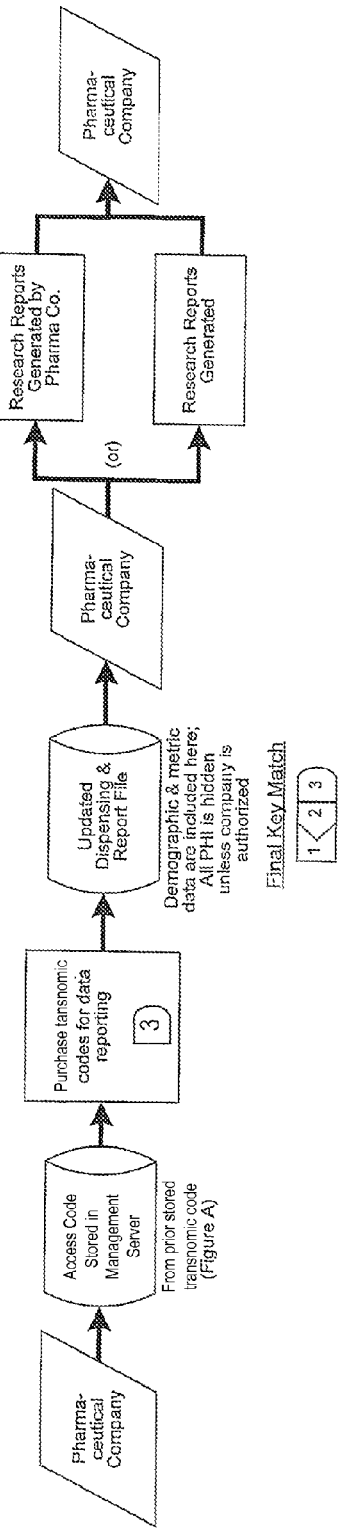

METHOD AND SYSTEM FOR TRACKING GOODS

CROSS REFERENCE TO RELATED APPLICATION[S]

This application is a continuation-in-part of the earlier U.S. Utility patent application to entitled "NOVEL METHODS AND SYSTEMS FOR PRESCRIBING SAMPLE PRESCRIPTIONS," Ser. No. 13/278,746, filed Oct. 21, 2011, now pending, which is a continuation of the earlier U.S. Utility patent application to entitled "NOVEL METHODS AND SYSTEMS FOR PRESCRIBING SAMPLE PRESCRIPTIONS," Ser. No. 11/908,397, filed Sep. 11, 2007, now U.S. Pat. No. 8,078,479, which is a 371 filing of the earlier PCT Patent Application entitled "NOVEL METHODS AND SYSTEMS FOR PRESCRIBING SAMPLE PRESCRIPTIONS," application number PCT/US2006/09058, filed Mar. 13, 2006, which claims priority to U.S. Provisional patent application to entitled "NOVEL METHODS AND SYSTEMS FOR PRESCRIBING SAMPLE PRESCRIPTIONS," Ser. No. 60/660,780, filed Mar. 11, 2005, the disclosures of which are hereby incorporated entirely herein by reference.

BACKGROUND OF THE INVENTION

1. Technical Field

This invention relates generally to a system for tracking pharmaceuticals and implantable devices, and more particularly to a method and system for using a transnomic code to track pharmaceuticals and implantable devices throughout a life-cycle of the same.

2. State of the Art

Conventionally, there are various ways in which companies and systems operate to track inventory and/or a product's life-cycle. Some of these conventional systems utilize a code system, wherein the code is attached to the product and provides static information with regard to the product, but doesn't track movement from the manufacturer to the point of sale or distribution (i.e., through the entire product life cycle). With these static codes, there is a finite amount of information that can be included with the code, such information being added at the time the code is associated with the product. Further, the code used does not provide for the opportunity to add additional information with regard to the effects of use of the product. This is particularly the case with regard to pharmaceuticals. Conventionally, these codes include a product identification bar code, a quick response code or the like.

Accordingly, there is a need in the field of codes to track the entire product life-cycle, for a code that is dynamic and extensible.

BRIEF DESCRIPTION OF THE DRAWINGS

These and other features, aspects, and advantages of the present invention will become better understood with regard to the following description and accompanying drawings where:

FIG. 4A-F is a flow diagram of a further embodiment of the transnomic code system process in accordance with the present invention.

DETAILED DESCRIPTION OF EMBODIMENTS OF THE INVENTION

A. System Architecture

Figure 1:
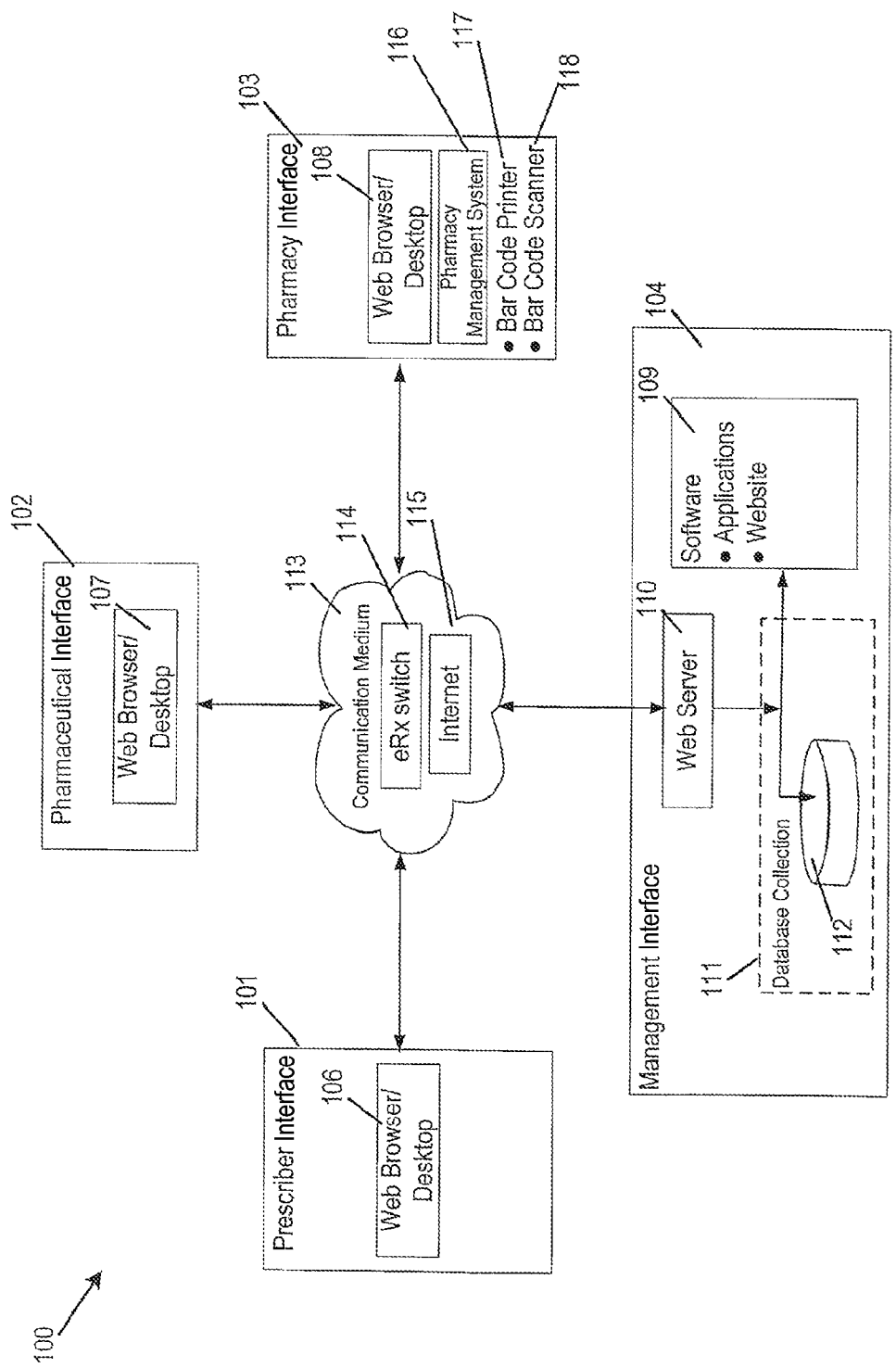
FIG. 1 is a diagrammatic illustration of the general architecture of one embodiment of a transnomic code system of the present invention.

FIG. 1 illustrates one non-limiting embodiment of the general architecture of a transnomic code system 100 (herein also referred to as "TCS") that operates in accordance with the present invention. The TCS 100 includes a prescriber interface 101, a pharmaceutical interface 102, a pharmacy interface 103 and a management server 104, that communicate via communication mediums 113, such as an electronic prescribing switch 114, and the Internet 115. In embodiments, users access the system through one of the interfaces to append information sets to the transnomic code, the management server 104 automatically adds information to the transnomic code, or both a user and the management server 104 may add information to the transnomic code.

1. Prescriber Interface 101

The prescribing interface 101 may be implemented using any type of computing device for operating a web browser 106. The computing device is defined as a device that enables a user to browse a remote web site through the communication medium using, for example, a web browser. Examples of the computing device include a desktop computer, a lap top computer, a personal digital assistant, an interactive wireless communications device, a handheld computer, a computer server, smart phones, tablets, mobile computing devices or the like, which connects with the communication medium. Additionally, the computing device may include any number of known peripheral devices that cooperate with the computing device, such as a printer, a scanner, a bar code scanner, facsimile machine and the like.

The prescriber interface 101 may be accessed from anywhere, and in particular embodiments are accessed where prescriptions are prescribed, such as a medical private practice, a hospital, or a clinic. The prescriber may still be located anywhere a mobile device can access the TCS 100 on a wireless network, such as but not limited to, WiFi, 3G, or 4G network where they can initiate a prescription. In general, the prescriber interface 101 enables a prescribing entity, such as a physician, to access the management server 104 to prescribe a medication to a patient via an electronic prescription switch and to append data to the transnomic code. The transnomic code is paired with the electronic prescription when completed in the prescriber interface 101 and sent into the communication mediums 113. The paired data may then be split into two transmissions at the management server 104, with the electronic prescription being submitted to the electronic prescription switch (denoted as eRx switch) 114 for ultimate delivery to the chosen pharmacy. A switch refers to an organization that receives live pharmacy claims from a pharmacy management system and then routes them to the appropriate claims processor for pharmacy benefit manager ("PBM") functions. Once the claims processor adjudicates the claim and sends a response, the switch also returns the adjudicated claim from the claims processor to the management server 104 from where it originated. The transnomic code is updated with the new information received at the management server 104 during this step and is then stored to be made available to other users with appropriate access.

2. Pharmaceutical Interface 102

The pharmaceutical interface 102 is implemented using one or more computing devices for operating a web browser 107. The pharmaceutical interface 102 may be accessed from anywhere and particularly at a company's physical facilities. It is also contemplated that the pharmaceutical interface 102 may be accessed from a computing device that comprises a main server located at a pharmaceutical company's facilities, which may be remotely accessed by other computer devices. For example, pharmaceutical sales representatives may access the pharmaceutical company's server via a wireless personal digital assistant device, which advantageously enables the sales representatives to access the management server 104 remotely. Alternatively, the wireless personal digital assistant device may be capable of accessing the management server 104 directly without having to first access the pharmaceutical company's server.

The pharmaceutical interface 102 contains within it various levels of permission to assign drugs, patient terms, and physicians to transnomic codes. Specifically, it is contemplated that an appropriate party at the pharmaceutical company has protected administrative entry screens to control the drug chosen for available transnomic codes. The party also controls the patient terms (e.g. free, discounts off cash price, reduction of copay, or patient contribution, number of refills, etc.) and establishes parameters for the transnomic code distribution for a specific coupon or marketing discount or sampling program.

3. Pharmacy Interface 103

The pharmacy interface 103 is also implemented using one or more computing devices for operating a web browser 108. The pharmacy interface 103 may be accessed from anywhere, and particularly at a location that dispenses prescriptions and sample prescriptions. The pharmacy interface 103 is capable of accessing the management server 104 and receiving information sent from the management server 104, such as emails, via the communication medium 113. The pharmacy interface 103 may also be used to append data to the transnomic code in the management server 104 and access the stored data for that transnomic code. The pharmacy interface 103 may also contain an application to receive electronic prescriptions from the electronic prescription switch 114 in addition to the tools to access the management server 104.

4. Management Server 104

In general, the management server 104 provides functionality for managing transnomic codes utilized in the TCS 100. Typically, the management server 104 is operated by a business entity that handles various prescription order processing tasks, collections, distribution of information and customer service tasks associated with the TCS 100. The management server 104 may include software 109 that implements an online registration process (not shown) for enabling other entities, such as physicians, physician practice groups, hospitals, clinics, pharmaceutical companies, pharmacies, and so forth, to register as members. The management server 104 contains administrative interface screens which allow various users with the appropriate privileges to establish terms to allow users to append data to the transnomic codes, as referenced above under Section 2, 'Pharmaceutical interface 102.'

The management server 104 may identify customers using any appropriate method, such as cookie retrieval or log-in procedures. Additionally, communications between devices of the TCS 100 preferably use an authenticated certificate in accordance with governmental regulations, such as U.S. Drug Enforcement Administration ("DEA") policies.

The management server 104 illustrated in FIG. 1 includes components that may be used to implement the above-described features. The exemplary management server 104 includes a web server 110, which accesses a database collection 111 that includes a database of sample prescription information 112 and related content. The web server 110 also manages a web site accessible via the communication medium 113. The web server 110 may also process requests made with an appropriate permission level or de-coding key for the prescription information contained in the transnomic code, review and authenticate the prescription information, and send and receive prescription information to and from the prescriber interface 101, the pharmaceutical interface 102 and the pharmacy interface 103 via the communication medium 113. The information may be used to provide prescriptions to patients via submission to the electronic prescribing switch 114, track the prescriptions through to the endpoint of patient pick-up at the pharmacy and generate prescription marketing reports among other functions.

The web server 110 communicates with management server software 109 as well as the database collection 112 to manage the prescription process and to provide prescription related information to appropriate users. Additionally, the management server software 109 generally implements the functions of the management server 104, including releasing information, populating the database 111 and operating the management server web site.

a. Database Collection 111

Figure 3:
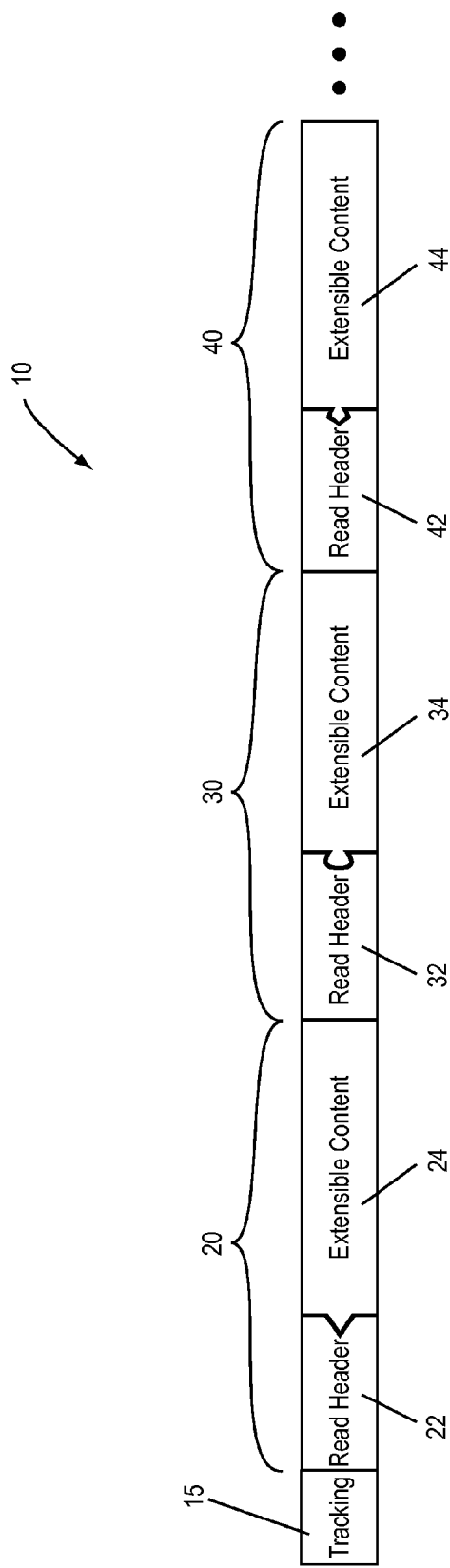
FIG. 3 is a diagrammatic illustration of an embodiment of a transnomic code and illustrates a flow of information among components of the present invention.

The database collection 111 illustrated in FIG. 1 includes the database 112 for storing transnomic code related information. The database 112 contains a plurality of files, each designated by a unique encrypted transnomic code corresponding to a particular medication. In other words, each medication produced by a pharmaceutical company that uses the TCS 100 has a corresponding transnomic code in the database 112, wherein the transnomic code for each medication may be directed at particular lots of medication, particular prepackaged medications, and the like. The transnomic code may be randomly generated or may be generated using a convention where the transnomic code has specific meaning. Specifically, in the latter instance, a person with knowledge on how to read the transnomic code may obtain information about the corresponding medication by analyzing the transnomic code. For example, referring to FIG. 3, the transnomic code 10 may have a tracking code 15 that comprises static information with at least one read header 22 and extensible content 24, wherein the read header 22 provides instructions relating to the extensible content 24 that identifies other information that is dynamically added over the product life-cycle as well as additional information deriving from effects after the use of the product.

The transnomic code 10, for example, is a type of "living-code" that is both the extensible and dynamic embodiment of the information contained within the transnomic code through time as more information is added to it, reflecting various events in the product life-cycle as well as adding information deriving from effects after the use of the product. This is the key distinction from many other industry standard methods of describing codes, such as, but not limited to, bar-codes or product labels, in which a fixed or static set of fields, or a fixed/static format is utilized. Instead, the transnomic code 10 is infinitely flexible over the product life-cycle and pattern of use. This flexibility of the transnomic code 10 is reflected in that according to embodiments, at various times, the management server may be accessed by different parties through particular interfaces to both retrieve and add information in real time and date to the transnomic code 10 electronically.

For the sake of clarity, consider each information set 20, 30, 40 and so on added by an interface of the TCS 100 to the transnomic code 10 has two parts, a read header 22, 32, 42 respectively, as well as extensible content 24, 34, 44. The read header 22, 32, 42 is information that is relevant to the interpretation, or security, of the information and extensible content 24, 34, 44 forms the rest of the transnomic code 10. Each information set 20, 30, 40 is associated to a particular transnomic code 10 by use of and reference to the tracking code 15. So, for example, a transnomic code 10 may be utilized by the TCS 100, wherein the transnomic code 10 corresponds to a health care product used by a consumer, such as a pharmaceutical product. The pharmaceutical product and consumer information is governed by HIPAA and accordingly, to the transnomic code 10 also contains sensitive information governed by HIPAA privacy rules and contains Protected Health Information ("PHI") with respect to who has what level of access to clinical outcomes information on the use of that pharmaceutical product.

In this example above regarding pharmaceutical products, the transnomic code 10 with a tracking code 15 may include a first information set 20 having a read header 22 and extensible content 24. The read header 22 may contain specific code instructions regarding how the information in extensible content 24 is to be accessed, unpacked, read and interpreted, and further may govern access to subsets of information in the extensible content 24 to users based upon user access privileges to a particular set or subset of information. The extensible content 24 may include information regarding the pharmaceutical associated with the transnomic code 10, the type and dosage of the pharmaceutical, pharmaceutical company that manufactured the medication, the location of manufacture, the lot number, NDC, other industry standard nomenclature related to a pharmaceutical product, and the like.

The transnomic code 10 may then have added to it another information set 30 having a read header 32 and extensible content 34. The read header 32 may contain specific code instructions regarding how the information in extensible content 34 is to be accessed, unpacked, read and interpreted, and further may govern access to subsets of information in the extensible content 34 to users based upon user access privileges to a particular set or subset of information. The extensible content 34 that may include prescription information, the condition or diagnostic code of the patient that is receiving the prescription and the like.

Further, the transnomic code 10 may further have third information set 40 having a read header 42 and extensible content 44 added to the transnomic code 10. The read header 42 may contain specific code instructions regarding how the information in extensible content 44 is to be accessed, unpacked, read and interpreted, and further may govern access to subsets of information in the extensible content 44 to users based upon user access privileges to a particular set or subset of information. The extensible content 44 of the information set 40 may include health outcomes information with a read header 42 that defines the ability of any other user through the TCS 100 to access the extensible content 44 in that transnomic code 10 based on permissions according to HIPAA privacy rules. Each of the information sets 20, 30 and 40 are combined to form an embodiment of the transnomic code 10. It will be understood that other types of information sets may be added to the transnomic code 10, even after the dispensing and patient pick-up information of the product associated with the transnomic code 10.

The read header 22, 32, 42 of each information set 20, 30, 40 may also include a time stamp, which permits the information sets 20, 30, 40 to be added asynchronously to the transnomic code 10. For example, the various interfaces associated TCS 100 with the various access and user points may have different latencies with respect to how they will add/update information, but because of the time stamp it does not matter what order the header/information sections are added, the transnomic code 10 can at any time be read and unpacked, and the contained information placed in its appropriate time series sequence as needed.

In general, the read header 22 may contain specific code instructions to the management server regarding how the information in extensible content 24 is to be accessed, unpacked, read and interpreted. The read header 22 may also allow access to subsets of information to users based upon user access privileges to a particular set or subset of information. The TCS 100 may grant access to the entire set of information contained within the transnomic code 10, or may only allow certain users access to information going forward in time from their access point along the chain of information that was built over the life-cycle of the product. On the other hand, some users may only be allowed access to retrospective analysis of information from a certain historical point in the code's development. This could be useful, for example, where an image file reflecting some particular assessment of the product or the outcomes it produces (quality assessment/quality control image of the product, such as for non-destructive testing of an orthopedic implant, or a radiographic image of tumor for an outcomes assessment) needs to be read with a specific piece of software or a certain compression standard. Accordingly, the "read header" is particularly useful because it allows various users through defined interfaces to access the management server to append information to the transnomic code, with the information in a read header on how to read the content of the extensible content added within the transnomic code, so that other users may have access to that content directly, without needing separate updating and communication between users. This is not only important across different types of users reflecting different interests and needs in the particular transnomic code at a point in time, but also creates robustness in the ability of the users through the management server to interpret the extensible content through time. Given that some product life-cycles may last for many years or decades (such as implantable devices in orthopedics or cardiac and diabetic implant devices), this can be quite important.

In an exemplary embodiment, the extensible content is populated by inputting information into the TCS 100 by the various interfaces, such as prescriber interface 101, the pharmaceutical interface 102, the pharmacy interface 103, and/or from another source or interface, such as a pharmacy benefit manager or electronic prescription switch, that has the desired information. The information may be inputted in any number of ways known by those skilled in the art, such as automatic uploading when a triggering event occurs during the life-cycle of the product or manual inputting of the information.

In connection with the database collection 111, in one embodiment, there may be several processes (not shown) such as ID generators, number generators and temporary storage units that may work with the database collection. Furthermore, it is recognized that the database collection 111 may be implemented using a variety of different databases such as relational databases, flat file databases, or object oriented databases. Moreover, while the database collection depicted in FIG. 1 is comprised of one database 112, it is recognized that in other embodiments, the database collection may include other databases. In addition, the database collection may be implemented as a single database with separate tables or as other data structures that are well known in the art such as linked lists, stacks, binary trees, and so forth.

5. Communication Mediums 113

The communication mediums 113 include an electronic prescription switch 114 and the Internet 115, though a wide range of interactive communication mediums may be employed in the TCS 100 as is well known to those skilled in the art via encrypted, HIPAA compliant encoding.

6. Other Embodiments

While FIG. 1 illustrates an embodiment wherein the management server 104 primarily implements the TCS process, it is recognized that in other embodiments, the management server 104 may include or work in conjunction with one or more third parties (not shown) to provide the transnomic code service. In some embodiments, the third party web site may receive requests for prescriptions, samples and/or send prescriptions or sample prescriptions to the pharmacies. In other embodiments, a pharmacy benefit manager may be central to communicating data between the management server and the users that interact with the transnomic code along the chain to a patient receiving a pharmaceutical. In another embodiment, a prescriber may access and request electronic e-sampling coupons and attach them electronically to their prescription, forming another example of the dynamic nature and options that prescribers would have in using the Transnomic Coding System. It should be understood that embodiments of the transnomic coding system allow for the addition of various types of information that may be pertinent in the tracking of goods and particularly in tracking pharmaceuticals along the chain of custody of the those goods. It further allows the tracking association of information regarding the goods to be accessed by individuals to provide them with metrics or measurements by which to make determinations regarding results of the use of the goods, such as the effectiveness of a pharmaceutical for a particular patient, a particular illness, condition or the like. It further allows for analysis and aggregation of utilization data, allowing stake holders within the supply chain to monitor use, delivery, and dispensing information so as to further develop analytics and prediction models for future utilization and stocking of the supply chain and/or the pharmacies so as to avoid or reduce the likelihood of over stock or under stocking of products and medications in the supply chain.

Furthermore, although the embodiments described herein use web site technology to disseminate information, a variety of electronic dissemination technologies may be used.

In addition, although the TCS 100 is described using "a" management server 104, it is recognized that the management server 104 may comprise multiple different sites.

B. Process Using the Transnomic Code System 100

Figure 2:
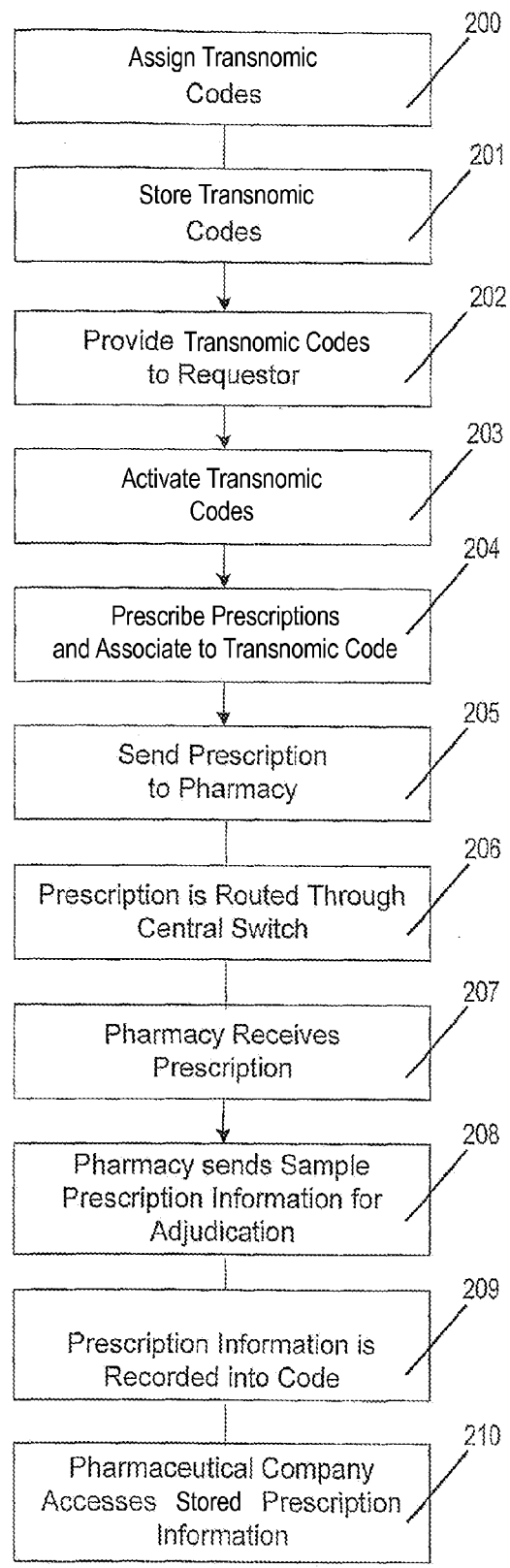
FIG. 2 is a flow diagram of one embodiment of the transnomic code system process in accordance with the present invention.

A description of a pharmaceutical use of the transnomic code system 100 is described with particular reference to FIG. 2. In a step 200, a pharmaceutical company, via the pharmaceutical interface 102, assigns a transnomic code to a product and stores the same in the management server 104. In an exemplary embodiment, the pharmaceutical company uses the pharmaceutical interface 102 via web browser 107 to accesses the web site of the management server 104. Once logged into the web site, the web site provides an option for the pharmaceutical company to assign a transnomic code to a product. Additionally, the web site prompts the pharmaceutical company to submit information about the product that will be used in conjunction with the transnomic codes. This information may include the lot number, the corresponding medication type, the terms available for the patient, and any other pertinent information as determined by the industry (e.g., NDC number) to establish a base for a transnomic code for the product. In a step 201, the management server 104 stores a number of transnomic codes corresponding to the number of products assigned in the step 200. An alternate mode of generating transnomic codes is a virtual "infinite" number of transnomic codes for the pharmaceutical company to activate sequentially. The management server 104 also stores each transnomic code in the database 112. Thus, each transnomic code corresponds to one product that the pharmaceutical company plans to distribute comprising and matching with a single prescription. Furthermore, information obtained during the step 200 is populated into the corresponding transnomic code to build the extensible transnomic code.

In a step 202, the management server 104 provides the transnomic codes to the requesting pharmaceutical company. In an embodiment, the transnomic codes are provided to the pharmaceutical company, wherein the management server 104 may be accessed by a pharmaceutical company through a pharmaceutical interface 102. The pharmaceutical company then has the ability to associate the transnomic codes to particular products. In other embodiments, the pharmaceutical interface 102 may be capable of downloading the list of transnomic codes or otherwise accessing the list of transnomic codes via the management server web site.

In a step 203, the pharmaceutical company activates the transnomic codes and the codes follow the product through the entire chain of custody. Accordingly, the transnomic code is a "living code" that is both an extensible and a dynamic embodiment of the information contained within the code through time as more information is added to it, reflecting various events in the product life-cycle as well as adding information deriving from effects after the use of the product. The transnomic code as described previously is created through the TCS 100 at the request of the pharmaceutical company, and the codes are stored on the management server 104. As information is added, the transnomic code stored on the management server 104 is updated and stored on the management server 104. As will be discussed, authorization is given to particular individuals to access the transnomic codes stored on the management server 104 and add information to the transnomic code, in order to further build the code and accurately reflect the life of the product from manufacture to dispensing. This is the key distinction from many other industry standard methods of describing codes, such as, but not limited to, bar-codes or product labels, in which a fixed set of fields, or a fixed format, of descriptor is defined, and the fields are filled by information as available. Instead, the transnomic code is indefinitely flexible over the product life-cycle and pattern of use. At various times, as described herein, the management server is accessed by different parties through corresponding interfaces, wherein the parties can both retrieve and add information to the transnomic code electronically.

In a step 204, medications are prescribed to a patient. Here a patient visits a physician whom was previously allocated sample codes as discussed above. Alternatively, the patient-physician examination may be performed via a real time video conferenced telemedicine appointment. The physician/prescriber examines the patient and determines that the patient should take a particular medication. The physician may then access the management server 104 through the prescriber interface 101 and prescribe a pharmaceutical product.

There are a number of alternative ways in which the physician can prescribe the prescription. In one embodiment, the physician accesses the management server 104 web site, app, or third party e-prescribing entity if the prescriber interface 101 includes access to both. The physician then navigates to an application of the web site that enables the physician to "e-prescribe" the prescription. In general, "e-prescribe" means that the physician can use a computer device to transmit the prescription to a medication dispensing facility, such as a pharmacy.

The "e-prescribe" application prompts the physician for information required to fill the prescription. This information may include the desired dispensing location (e.g. pharmacy location), patient information (e.g. name, age, sex, and other identifiers) and sample code, if any. The physician then submits the prescription, and the information is routed to the management server 104. The management server 104 may then perform any number of processes, including adding content to the transnomic code in the database 112 and checking the database collection 111 to determine whether or not the patient was recently prescribed similar medication that may indicate unlawful conduct (e.g. "physician shopping"). In other embodiments, the TCS 100 also may authenticate the prescriber by verifying that the prescriber is lawfully able to prescribe the medication by referencing the prescriber's DEA or National Provider Identifier (NPI) number designation.

In a step 205, the prescription is sent to a participating dispensing location. In an exemplary embodiment, the "e-prescribe" application transmits the prescription from the management server 104 to the pharmacy interface 103 via the communication mediums 113. The communication mediums may, or may not include a combination of the electronic prescription switch 114 and the Internet 115. In alternative embodiments, the prescription may be sent via fax.

In a step, 206, before reaching the pharmacy interface 103, the prescription is routed to an organization that administers the electronic prescription switch 114. The transmission to the electronic prescription switch 114 may be initiated by an e-prescribing application with direct access to the switch 114 or through the management server via the Internet 115.

In a step 207, the pharmacy interface 103 receives the electronic prescription, triggering any number of actions. If the electronic prescribing switch 114 has accessed the appropriate PBM prior to delivery of the sample code and prescription to the pharmacy interface 103, then the pharmacy may dispense the prescription and complete a dispensing confirmation to send to the PBM. If the PBM has not yet been accessed, the pharmacy interface 103 instructs a pharmacy's practice management system, which may or may not be part of the pharmacy interface 103, to send the prescription to the appropriate PBM for adjudication. In general, in the step 208, the TCS 100 preferably coordinates with a pharmacy benefit manager verification that the prescription is valid (e.g. not forged), authenticates that the prescription originated from the management server 104 and determines whether or not the sample prescription is likely to cause an adverse reaction with other medications taken by the patient. In one embodiment, the pharmacy interface 103 receives a copy of the prescription in the form of an encrypted email or faxed sample prescription having a bar code that can be scanned at the pharmacy.

In a step, 209, the pharmacy interface 103 transmits prescription information to the management server 104 via the PBM. In an embodiment, the pharmacy interface 103 may automatically transmit the desired information when the prescription is delivered to the patient as an additional transmission. For example, the pharmacy interface 103 may produce a bar code (e.g., print a bar code label via a printer 117) that is affixed to a package (e.g., container) of the prescription. Desirably, the bar code corresponds to the transnomic code for the prescribed medication and stored on the management server 104. Thus, after a pharmacy employee scans the bar code with a bar code scanner 118 when a patient picks up the prescription, the pharmacy interface 103 recognizes the bar code and automatically updates the transnomic code on the management server database 112 with additional prescription information, such as the date and time the patent picked up the prescription. Alternatively, instead of using a bar code and bar code scanner, the pharmacy employee may enter a prescription identification number that corresponds to the prescription into the pharmacy interface 103. This allows for the collection of data specific to the patient receipt of the prescription, as adjudication through the PBM is often asynchronous to the time of pickup by a patient. A similar process integrating shipment delivery data may be used to support the collection of the data for prescriptions received at home by a patient.

It is desired that the pharmacy interface 103 assist in reporting information about the prescribed medication and the patient by interacting with a designated PBM. Typically, the PBM functions to manage eligibility, conduct utilization reviews for appropriateness of a therapy, and perform settlements between pharmacies, pharmaceutical companies and insurance companies. In this embodiment the PBM also is a primary conduit for the collection of data that is ultimately added to the transnomic code.

In step 209, the prescription information collected by the PBM is delivered back to the TCS 100 for addition to the transnomic code stored in the database 112. The PBM or the electronic prescription switch 114 may be used to analyze drug interactions between medications prescribed to patients.

In an embodiment, the pharmacy interfaces 103 have "keys" that enable the pharmacy interface 103 to read the prescription submitted by the management server 104. If the pharmacy interface 103 does not have the appropriate key, then the pharmacy interface 103 cannot open the sample prescription. Also, the pharmacy interface 103 may be given a unique pharmacy identifier. When the transnomic code is accessed by the pharmacy interface 103, the unique pharmacy identifier is automatically sent to the management server 104. If the pharmacy identifier matches pharmacy information populated in the corresponding transnomic code (step 204), then the management server may send a "key" code to the pharmacy interface 103 that enables the pharmacy interface 103 to open the prescription. This is independent of verifications made on an electronic prescription by the electronic prescribing switch 114 or a PBM. Regardless of the pharmacy interface's 103 ability to open a prescription, it is still able to adjudicate the prescription with a PBM by other means, assuming the pharmacy has received an electronic prescription for the sample.

In a step 210, the pharmaceutical company, having the pharmaceutical interface 102, obtains information from the transnomic code. In general, the pharmaceutical company purchases information from the management server 104, which was acquired for the transnomic codes that were allotted to the pharmaceutical company in the step 200. In an embodiment, the pharmaceutical company accesses the management server web site via the pharmaceutical interface 102 and navigates through the web site to a data report application. Here, the pharmaceutical company or authorized third party can download information stored in the database 111 after paying a fee to the management server entity. In another embodiment, the pharmaceutical company or other subscribing company is provided with a unique identification number, after paying a fee, which allows them to access the sample code files. Preferably, the pharmaceutical company has access limited to only non-confidential information (in other words, no PHI). For example, the pharmaceutical company or authorized third party may be denied access to private patient information, such as social security numbers or names, but has access to non-confidential information such as demographic and metric data. Thus, the pharmaceutical company has access to valuable marketing information, but yet does not violate a patient's confidentiality/HIPAA rights.

Further, in some embodiments, a prescriber may also access the transnomic code through a prescriber interface 102. The prescriber may then generate a report through use of a data report application. The report may be delivered by the TCS 100 after the prescriber pays a fee.

Although the present invention has been described in considerable detail with reference to certain preferred embodiments thereof, other versions are possible. For example, an embodiment uses the sample prescription system process shown in FIG. 4 A-F. Also, many of the steps described herein may be accomplished via mail, fax or other communication method instead of the Internet. Additionally, it is contemplated that the embodiments of the present invention can be used with regular prescriptions as well as sample prescriptions.

Therefore, the embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims.

The invention claimed is:

1. A method of managing and tracking pharmaceutical products through a chain of custody performed by a computing device, the method comprising:
automatically creating a transnomic code in response to an electronic request by a contracting user to a management server, wherein the transnomic code comprises a static tracking code and a plurality of information sets, each information set comprising a read header and extensible content;
assigning the transnomic code to a pharmaceutical product, wherein the contracting user accesses the management server through a pharmaceutical interface via an Internet connection;
automatically storing the transnomic code in a database of the management server, wherein the plurality of information sets of the transnomic code are appended longitudinally through time and comprise a variety of information records associated with the pharmaceutical product, wherein the read header provides a specification to read and interpret the extensible content corresponding to that read header, allowing the appending of information sets corresponding to different data standards and formats from different systems and different times;
prescribing the pharmaceutical product to a patient by a prescriber and automatically electronically updating the transnomic code assigned to the pharmaceutical product with a read header and extensible content comprising patient and prescription information, including a chosen pharmacy, wherein the prescriber accesses the management server through a prescriber interface via an Internet connection and the transnomic code is paired with the electronic prescription for transmission;
splitting the paired data into two transmissions at the management server and submitting the electronic prescription to an electronic prescription (eRx) switch for ultimate delivery to the chosen pharmacy;
authenticating that the prescribed pharmaceutical is not similar to a medication recently prescribed to the patent or is not likely to cause adverse reaction with other medications, wherein the transnomic code provides information regarding the prescribed pharmaceutical for determining drug interactions;
automatically electronically sending the prescription from the management server to the chosen pharmacy via the eRx switch, wherein the pharmacy is an entity separate from the prescriber;
dispensing the pharmaceutical product to the patient by the pharmacy; and
automatically electronically updating the transnomic code with a read header and extensible content comprising prescription tracking information by the pharmacy, wherein the pharmacy accesses the management server through the pharmacy module via an Internet connection.

2. The method of claim 1, wherein the contracting user is a pharmaceutical company.

3. The method of claim 1, further comprising electronically updating the transnomic code by the prescriber with information relating to results of use of the pharmaceutical product by the patient.

4. The method of claim 1, further comprising accessing the updated transnomic code stored on the management server by the contracting user, wherein the contracting user accesses the management server through the pharmaceutical interface via an Internet connection.

5. The method of claim 4, further comprising generating a report with information in the transnomic code, wherein the report is electronically requested by the contracting user through the pharmaceutical interface.

6. The method of claim 5, further comprising paying a fee by the contracting user to generate the report.

7. The method of claim 4, wherein the report comprises only non-confidential information.

8. The method of claim 1, further comprising accessing the updated transnomic code stored on the management server by the prescriber, wherein the prescriber accesses the management server through the prescriber interface via an Internet connection.

9. The method of claim 4, further comprising generating a report with information in the transnomic code, wherein the report is electronically requested by the prescriber through the prescriber interface.

10. The method of claim 5, further comprising paying a fee by the prescriber to generate the report.

11. A method of managing and tracking pharmaceutical products through a chain of custody performed by a computing device, the method comprising:

automatically creating a transnomic code in response to an electronic request by a contracting user to a management server, wherein the transnomic code comprises a static tracking code and a plurality of information sets, each information set comprising a read header and extensible content;

assigning the transnomic code to a pharmaceutical product, wherein the contracting user accesses the management server through a pharmaceutical interface via an Internet connection;

automatically storing the transnomic code in a database of the management server, wherein the plurality of information sets of the transnomic code are appended longitudinally through time and comprise a variety of information records associated with the pharmaceutical product, wherein the read header provides a specification to read and interpret the extensible content corresponding to that read header, allowing the appending of information sets corresponding to different data standards and formats from different systems and different times;

prescribing the pharmaceutical product to a patient by a prescriber and automatically electronically updating the transnomic code assigned to the pharmaceutical product with a read header and extensible content comprising patient and prescription information, including a chosen pharmacy, wherein the prescriber accesses the management server through a prescriber interface via an Internet connection and the transnomic code is paired with the electronic prescription for transmission;

splitting the paired data into two transmissions at the management server and submitting the electronic prescription to an electronic prescription (eRx) switch for ultimate delivery to the chosen pharmacy;

authenticating the prescriber is lawfully able to prescribe the pharmaceutical product, wherein the transnomic code provides prescription information for verifying the prescriber;

automatically electronically sending the prescription from the management server to the chosen pharmacy via the eRx switch, wherein the pharmacy is an entity separate from the prescriber;

dispensing the pharmaceutical product to the patient by the pharmacy; and automatically electronically updating the transnomic code with a read header and extensible content comprising prescription tracking information by the pharmacy, wherein the pharmacy accesses the management server through the pharmacy module via an Internet connection, wherein:

each information set comprises a time stamp for asynchronous adding of information sets to the transnomic code, wherein the transnomic code comprises instructions for automatically reading, unpacking, and placing each information set of the transnomic code in its appropriate time series sequence.

* * * * *

UNITED STATES PATENT AND TRADEMARK OFFICE
CERTIFICATE OF CORRECTION

PATENT NO.        : 9,235,869 B2
APPLICATION NO.   : 13/710167
DATED             : January 12, 2016
INVENTOR(S)       : Eric Greenman and Bo E. H. Saxberg It is certified that error appears in the above-identified patent and that said Letters Patent is hereby corrected as shown below:

In the claims
In claim 1, Column 12, Line 18, the word "patent" should read "patient."

Signed and Sealed this
Fourteenth Day of June, 2016

Michelle K. Lee
*Director of the United States Patent and Trademark Office*